United States Patent
Flaction et al.

(10) Patent No.: US 8,655,618 B2
(45) Date of Patent: Feb. 18, 2014

(54) ACCELEROMETER AND METHOD FOR CONTROLLING AN ACCELEROMETER

(75) Inventors: Patrick Flaction, Chandolin-pres-Saviese (CH); Alex Bezinge, Saviese (CH); Jacques Quievre, Rozay en Brie (FR)

(73) Assignee: Myotest SA, Sion (CH)

( * ) Notice: Subject to any disclaimer, the term of this patent is extended or adjusted under 35 U.S.C. 154(b) by 269 days.

(21) Appl. No.: 12/674,094

(22) Filed: Feb. 18, 2010

(65) Prior Publication Data

US 2010/0211349 A1 Aug. 19, 2010

Related U.S. Application Data

(63) Continuation of application No. PCT/EP2008/060950, filed on Aug. 21, 2008.

(30) Foreign Application Priority Data

Aug. 23, 2007 (EP) .................................... 07114873

(51) Int. Cl.
*G01P 15/00* (2006.01)
*G01P 7/00* (2006.01)

(52) U.S. Cl.
USPC .......................................... 702/141; 702/142

(58) Field of Classification Search
USPC ........... 702/33, 41, 57, 141, 142; 73/488, 489
See application file for complete search history.

(56) References Cited

U.S. PATENT DOCUMENTS

| | | | |
|---|---|---|---|
| 4,699,379 A | 10/1987 | Chateau et al. |
| 4,824,103 A | 4/1989 | Smidt |
| 5,056,783 A | 10/1991 | Matcovich et al. |
| 5,184,295 A | 2/1993 | Mann |
| 5,474,083 A | 12/1995 | Church et al. |
| 5,476,103 A | 12/1995 | Nahsner |
| 5,788,655 A | 8/1998 | Yoshimura et al. |
| 6,148,280 A | 11/2000 | Kramer |
| 6,231,481 B1 | 5/2001 | Brock |
| 6,234,975 B1 | 5/2001 | McLeod et al. |
| 6,397,151 B1 | 5/2002 | Yamagishi et al. |
| 6,635,013 B2 | 10/2003 | Pfeffer |

(Continued)

FOREIGN PATENT DOCUMENTS

| | | |
|---|---|---|
| CN | 2930773 Y | 8/2007 |
| DE | 446302 C | 6/1927 |

(Continued)

*Primary Examiner* — Marc Armand
*Assistant Examiner* — Ricky Ngon
(74) *Attorney, Agent, or Firm* — Blank Rome LLP (57) ABSTRACT

A method for obtaining physiological muscle values of a user by a programmable accelerometer. In a first step, a user selects the type of test to be carried out. In a second step, a sequence of acceleration data is measured by the portable accelerometer during the test. In a third step, the end of the test is determined by the accelerometer by verifying a condition dependent on the type of test selected, and a sound signal is emitted. Finally, a value calculated on the basis of said successive measurements of the acceleration and dependent on the type of test selected is displayed.

20 Claims, 5 Drawing Sheets

(56) References Cited

U.S. PATENT DOCUMENTS

| | | |
|---|---|---|
| 2002/0028730 A1 | 3/2002 | Kaufman |
| 2002/0170193 A1 | 11/2002 | Townsend et al. |
| 2003/0163283 A1* | 8/2003 | O'Brien ................ 702/160 |
| 2004/0134274 A1 | 7/2004 | Hoggan et al. |
| 2005/0075586 A1 | 4/2005 | Jamsen |
| 2005/0172311 A1* | 8/2005 | Hjelt et al. ................ 725/10 |
| 2006/0191335 A1 | 8/2006 | Nose et al. |
| 2007/0027369 A1* | 2/2007 | Pagnacco et al. ........ 600/301 |
| 2007/0042866 A1 | 2/2007 | Skilken et al. |
| 2007/0172797 A1 | 7/2007 | Hada et al. |
| 2008/0249736 A1* | 10/2008 | Prstojevich ............. 702/141 |
| 2009/0062627 A1 | 3/2009 | Younger |
| 2009/0069722 A1 | 3/2009 | Flaction et al. |
| 2010/0204615 A1* | 8/2010 | Kyle et al. ............... 600/595 |

FOREIGN PATENT DOCUMENTS

| | | |
|---|---|---|
| DE | 4426302 A1 | 2/1996 |
| DE | 102004013997 A1 | 10/2005 |
| EP | 1834583 A1 | 9/2007 |
| GB | 2422790 A | 8/2006 |
| GB | 2447915 A | 10/2008 |
| JP | 2006271893 A | 10/2006 |
| JP | 2006320533 A | 11/2006 |
| WO | 03032826 A2 | 4/2003 |
| WO | 2005055815 A2 | 6/2005 |
| WO | 2005074795 A1 | 8/2005 |
| WO | 2007036611 A1 | 4/2007 |
| WO | 2007107491 | 9/2007 |
| WO | 2009024600 | 2/2009 |

* cited by examiner

ACCELEROMETER AND METHOD FOR CONTROLLING AN ACCELEROMETER

This application is a continuation of international application PCT/EP2008/060950, filed on Aug. 21, 2008, the content of which is enclosed by reference. It claims priority from European Patent Application EP07114873 filed on Aug. 23, 2007, the content of which is enclosed by reference.

TECHNICAL FIELD

The present invention relates to an accelerometer used for measuring physiological muscle parameters based on short tests.

STATE OF THE ART

There are many documents describing accelerometers for measuring sport performances. Most of the existing accelerometers are designed for exercises lasting a longer period of time, for example to evaluate the traveled distance or the calorie expenditure during a jogging session or a cycling tour. Other accelerometers connected for example to a gyroscope are linked to a device whose trajectory one wishes to determine, for example to practise a golf swing or a backhand in tennis. Furthermore, there are accelerometers used for measuring an impact in a combat sport. There are also fairly similar devices for detecting elderly people falling, the time they spend sitting, standing or lying down, etc.

None of these devices allows basic physiological muscle parameters such as strength, speed or power of a muscle group to be obtained.

U.S. Pat. No. 5,788,655 (Omron) describes a device designed to be fastened onto the body and provided with an accelerometer and with an LCD. The device continuously measures the wearer's movements to determine his level of physical activity and other values depending on the metabolism, such as the user's daily calorie intake. This type of device is useful for measuring more objectively the level of inactivity of patients. It is however not adapted for muscle training and for measuring short efforts, and does not allow for example the maximum power of a muscle group of the athlete to be measured.

WO2005074795 (Nokia) describes a measurement terminal provided with an accelerometer and fastened onto the body of an athlete. The measurement data are assessed to supply a value representative of the intensity of the exerted effort. Again, the aim is to determine the level of activity over a long period, for example a day or a week.

WO03/032826 (Philips) describes a comparable system provided with a three-axis accelerometer for determining the level of physical activity of a patient. The proposed device displays values such as the daily metabolic rate, the daily energetic output or the energy output induced by exercise. This device is thus useful for measuring accelerations over a period of several hours or even of several days.

U.S. Pat. No. 5,474,083 describes a system designed to monitor the load-lifting movements of a patient. The system uses electrodes for measuring the activity of the patient's muscles during the movement, as well as a load movement detector. An alarm is triggered in case of inappropriate movement. This system is useful for preventing accidents caused by incorrect load lifting or for having people practise lifting loads without injury. It is however not suited for measuring the athlete's muscular performance. Furthermore, the use of electrodes makes it inconvenient to use.

U.S. Pat. No. 6,148,280 (Virtual Technologies) describes a device provided with accelerometers and gyroscopes placed on the whole body of an athlete. The data supplied by several sensors are transmitted to a PC that allows the trajectory and other features of the movement to be analyzed. This system is complex, since it makes use of several sensors, including expensive and relatively fragile gonometers. The connection of the sensors to one another and with the external computer increases the cost of the device and makes it difficult to install. It is adapted for training precise movements, for example a golf swing, but does not allow the muscle power developed by the athlete during this movement to be determined directly.

DE4426302 describes an accelerometer used in combat sports for measuring the acceleration of the strike surface. The apparatus is not portable and is suited only to combat sports such as boxing, karate, etc. An external computer must be used to assess and display the results of the measurement. It is not programmable and can be used only for a single type of exercise.

US2006191335 describes a portable accelerometer intended notably for measuring the muscular force of the legs. One button enables the device to operate according to three distinct modes. In endurance mode, the device emits a series of beeps spaced in time; at each beep, the subject must walk faster, until the fastest walking speed is achieved. The device then determines the endurance of the subject, as well as other parameters, on the basis of acceleration data measured during the test.

In training mode, the device of US2006191335 proposes muscle training exercises by having the subject walk at variable speeds. There is no measurement of physiological muscle values in this mode.

In the final, leg-strength mode, the device of US2006191335 allows the subject's leg strength to be calculated by a walking exercise. The user starts this exercise by pressing on the START/STOP button and interrupts it by pressing on the same button. The end of the test is thus determined by the user and is not signaled by the device.

The patent application EP1834583 in the name of the applicant describes a portable accelerometer allowing the type of test to be carried out to be selected. After a calibration phase enabling the vertical position to be calibrated, an acoustic beep is emitted to invite the user to carry out the test. The sound signal can depend on the selected test and can furthermore be accompanied by a message on the device's display. The acquisition of a sequence of acceleration data then starts and ends after a predetermined duration, when the device's memory is full or when the user presses on a button on the device. It is also possible to interrupt the data acquisition automatically according to the measured data, for example when the device determines that the athlete has touched ground again after a jump. The athlete must however check the screen of the device to know whether the test is finished and if the movement can be stopped. Depending on the test carried out, such a visual verification is impossible or at any rate inconvenient.

WO2007036611 describes a bracelet provided with an accelerometer for measuring the muscular strength when lifting loads. This device allows a single type of test to be carried out, without emitting any sound signals to help the user during the test.

Other accelerometers used for measuring muscular parameters are also described in GB2422790 and in WO20005055815.

BRIEF SUMMARY OF THE INVENTION

One aim of the invention is to propose a versatile accelerometer, suitable for different tests and for calculating different values, as well as a control method adapted for this accelerometer.

One aim of the present invention is also to propose an improved accelerometer enabling physiological muscle values such as strength, power, speed etc. to be measured very easily, with simple and short tests.

In this text, a short test is understood as being a test lasting typically several minutes, for example a test including one or several jumps or load lifts, the total duration of the test preferably lasting at most several minutes. The inventive accelerometer must in particular be suitable for measuring physiological muscle parameters from tests involving several movements, for example a sequence of jumps, lifts, etc. according to a test program determined by the device and depending on the type of test.

The invention is based notably on the observation that most users do not know exactly what the procedure is for the different selectable tests and that they are for example unaware at which point they must or can execute a new movement (for example a new jump) and when the exercise is finished. It is thus necessary to aid the users during and at the end of the exercise, in order to ensure that the test is conducted correctly and that useless additional movements are avoided.

According to the invention, these aims are achieved notably by means of a method for obtaining physiological muscle values of a user by means of an accelerometer, wherein the method comprises the following operations:

selection, by the user, of the type of test to be carried out;
measurements of a sequence of acceleration data during the test;
emission of a sound signal at the end of the test, the end of the test being determined by verifying a condition dependent on the type of test selected;
displaying of a value calculated on the basis of said successive measurements of the acceleration and dependent on the type of test selected.

This method notably has the advantage of using a single programmable accelerometer for determining several values by means of highly diverse tests. Furthermore, the end of a test is determined automatically, with the aid of criteria that depend on the selected test. It is thus possible to avoid the constraints of devices that force the user to perform a manipulation to signal to the accelerometer that the acquisition of data must be interrupted and that the measured or computed values are to be displayed. The end of the test corresponds for example to the moment when the accelerometer has acquired sufficient acceleration data, depending on the type of test selected, for calculating and displaying the physiological values required depending on the type of test.

The device preferably enables at least two types of distinct tests to be carried out, the end of each type of test being signaled by an acoustic signal and being determined by verifying conditions dependent on the type of test.

BRIEF DESCRIPTION OF THE FIGURES

Examples of embodiments of the invention are indicated in the description illustrated by the attached figures in which.

EXAMPLES OF EMBODIMENTS OF THE INVENTION

Figure 1:
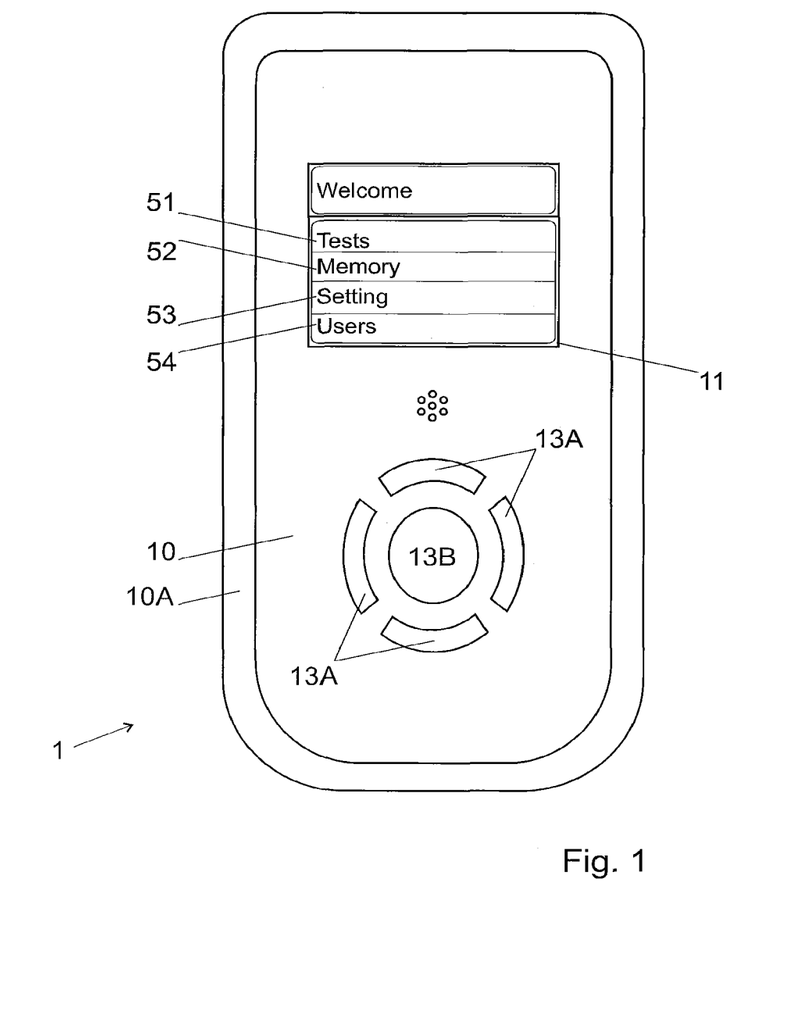
FIG. 1 illustrates an accelerometer for assessing the muscle power by means of short tests.

An example of accelerometer 1 according to the invention is illustrated in FIG. 1. The device 1 comprises a case 10, for example a plastic or eloxed aluminum case weighing less than 100 grams (including the contents) that the athlete can fasten, depending on the test carried out, on his body or on the lifted load with fastening means, for example a hook and loop tape, a strap etc., or by sliding it in a pocket or pouch. The case is preferably watertight and allows outdoor use and resistance to the athlete's sweat. A flexible protection 10A all around the case makes it shock-proof.

The device further includes a display 11, for example a matrix LCD, that allows the menu positions 51 to 54, the memory state 55, the battery state 56 as well as alphanumerical indications before, during or after the test to be displayed. Control elements 13 make it possible to navigate in the displayed menus, to select the options, to enter data and to select the results displayed. In the preferred embodiment illustrated, the control elements have four navigation buttons 13 A (up-down-left-right) and a button 13B for confirming the choices made.

Figure 2:
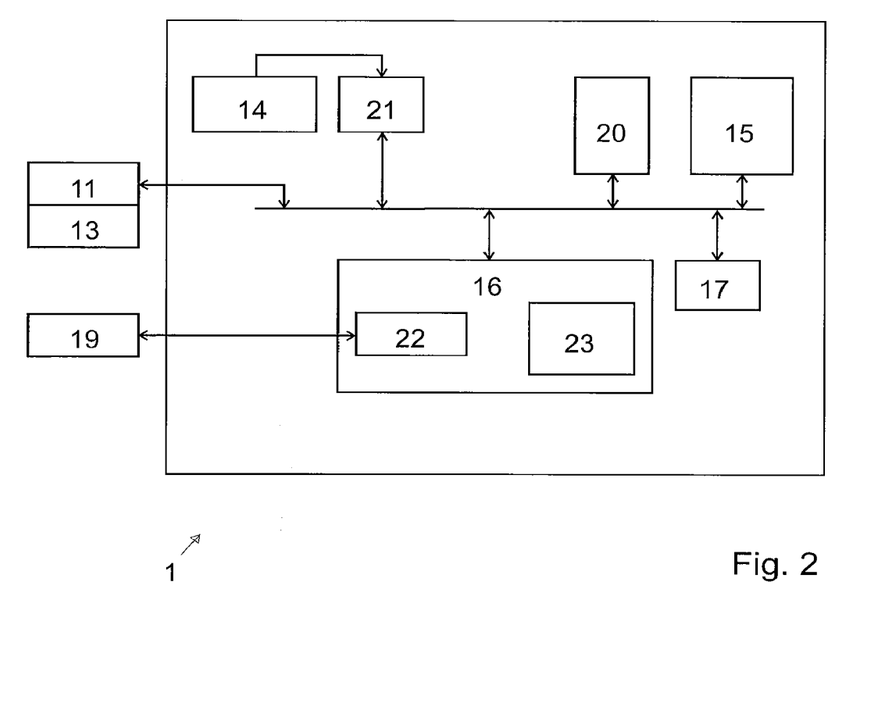
FIG. 2 is a block-diagram of the main electronic components of the accelerometer of FIG. 1.

FIG. 2 is a block-diagram illustrating the main electronic components of the device 1. In addition to the external elements already described in relation with FIG. 1, it includes an acceleration sensor, preferably a tri-axial sensor 14. The sensor is executed in the form of MEMS components and connected to an analog-to-digital converter 21 or integrating directly such a converter, to supply sequences of acceleration measurements along three axes. The sensor 14 can include one or several privileged axes, affording a measurement accuracy or resolution greater than the other axes. This privileged axis will for example be aligned approximately vertically when the device is in its normal position of use, in order to improve the measurement precision along the vertical direction. Using a triple-axis accelerometer makes it however possible to be free from the necessity of accurately adjusting the measuring axis with the privileged direction of acceleration.

Preferably, the accelerometer is further calibrated during its production in order to check offsets and other systematic errors along each axis and to introduce corresponding corrective factors into the accelerometer and/or in a software processing the accelerometer's data.

The device preferably lacks a gyroscope in order to reduce its cost, its energy consumption and the volume of generated data; using a single-axis or even a triple-axis gyroscope could however be considered for certain types of muscle power tests, for example in order to follow a movement in a three-dimensional space and comprising rotations.

The device 1 is preferably electrically autonomous and powered for example with the aid of a preferably rechargeable battery 15, for example through the USB port 19 or by removing it from its case. The battery 15 powers notably a microprocessor 16 or a microcontroller provided with a RAM and/or EEPROM memory 23. The microprocessor executes a program (firmware) preferably loaded in EEPROM, which can be replaced through the interface 19 or via a storage medium reader, for analyzing the measurement data supplied by the accelerometer 14 and control the display 11 in order to display the desired values. The accelerometer is thus programmable, by means of programs executed by the microprocessor 16.

The device 1 further comprises a real time clock (RTC) 20 that allows notably the time intervals Δt to be measured. The sampling period and the time intervals must be sufficiently short to measure jumps in a dynamic manner. Generally, intervals of 5 milliseconds are sufficient for relatively slow load tests, whilst intervals of 1 to 2 milliseconds maximum are preferable for jump tests that have much greater dynamics.

The device 1 also has a sound transducer 17 (buzzer 17 or loud-speaker) for generating control signals, error signals or other sounds. The transducer 17 allows instructions to be communicated to the athlete even when not looking at the screen; the signals emitted can be short signals (beeps, beep-beep, beeeep, etc.), polyphonic signals or voice signals pre-recorded or generated by a voice synthesizer. The acoustic signals can also be transmitted by a wireless interface towards headphones or a music player.

An input-output module (UART, Universal Asynchronous Receiver/Transmitter) 22 allows the microprocessor 16 to exchange data with external devices, for example for reprogramming the firmware or for transmitting measurement results or user parameters to a PC, a mobile phone or another external data processing device. The module 22 also makes it possible to enter at any time the parameters of new types of tests or to reprogram existing tests.

The module 22 is connected to an interface 19, for example a USB port, a wireless interface of the Bluetooth or other type, etc.

The accelerometer 1 makes it possible to measure accelerations along three axes, in particular the value of the acceleration in the assumed direction of the load displacement.

The sequence of acceleration data obtained during a test allows other values to be easily determined, in particular:

The force F=m·(g+a), g being the acceleration due to gravity and a the acceleration delivered by the athlete.
The speed v=∫a·dt.
The power $$P = \frac{dE}{dt} = F \cdot v = m \cdot a \cdot v,$$

for example the pulse power, thrust/pumping power, braking power, etc.
A distance, for example the height of a jump, by integrating the speed.
The duration of certain phases of a test, for example a contact time, a flight time, etc.
The index of reactivity.
The index of rigidity.
Other examples are given in the rest of the description or can be conceived by those skilled in the art.

The formulas above are valid in the case where the acceleration and the speed are parallel, for example during purely vertical displacements. In the case of non-parallel vectors, the calculation must be performed vectorially, or preferably by performing scalar products that take into account only the projection of the acceleration along the axis of displacement, for example along the vertical axis.

Furthermore, it is also possible to compute maximum or average forces, speeds and powers during a test, a movement or a phase of each movement. Thus, from a simple sequence of acceleration measurements, it is possible to deduce an entire series of physiological parameters, to compare them in time and to compare them between different athletes.

The calculations are preferably performed immediately after the acceleration data acquisition phase during the test. In one embodiment, at least some of the calculations are performed during the tests and/or during the pauses between two movements, for example in order to reduce the calculation time at the end of the test. In a preferred embodiment, the calculations necessary for determining the error conditions or the acoustic or visual signal emitted during the test are performed without awaiting the end, whilst the calculation of the other physiological muscle values is performed after the end of each test or of each movement in a test comprising several movements.

In one embodiment, the momentary speed for example is computed throughout the test in order to react, for example with an error signal, if the user moves a load in the wrong direction or does not execute the expected movement. The computations during the test also enable the different movements of a test and/or the different phases of a movement to be distinguished. Generally, the accelerometer can use an a priori knowledge of the measured or calculated values according to the test to aid the user and/or generate error signals if the values obtained do not correspond to a pattern depending on the test (for example if the speed is positive instead of being negative, if the accelerometer is not immobile, etc.).

It is also possible to approximate the speed, or other values, during the test and to recalculate these values more accurately at the end of the test, or between two movements.

Figure 3:
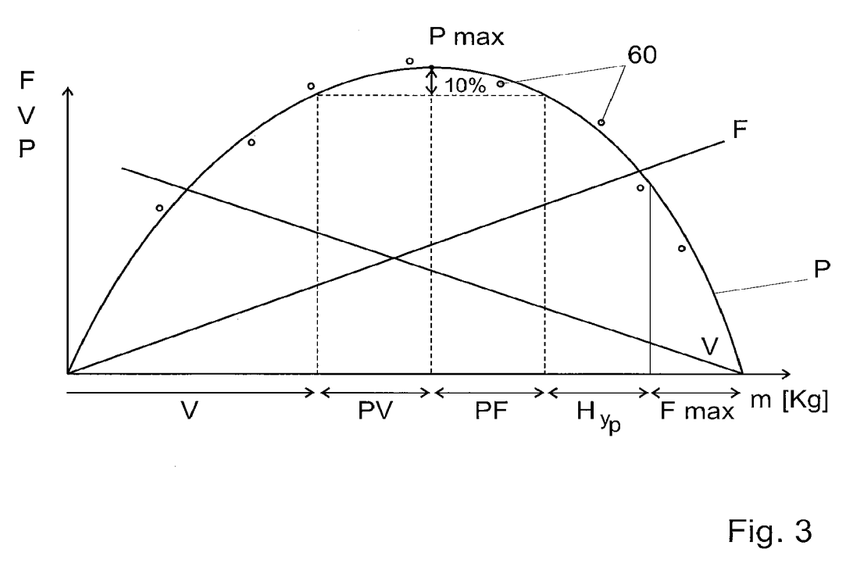
FIG. 3 illustrates the strength, speed and power an athlete can produce according to the load moved.

FIG. 3 illustrates diagrammatically a possible evolution of the force F, the speed V and the power P expended by an athlete lifting different loads of variable mass m. The gravitational force (m×g) exerted on the load used increases linearly with the load's mass. On the other hand, the lift speed V diminishes when the lifted mass increases; the athlete lifts light masses more quickly.

The power P during the effort thus goes through an optimum for a given value of the lifted mass m. The relation P=f(m) can be obtained for example by interpolation or extrapolation calculations from a series of tests (profile) carried out with variable loads, allowing the curve P to be obtained from the measurement results 60 illustrated.

This power curve that can be calculated or taken into account by the accelerometer is particularly useful in order to determine the load with which the athlete must train to obtain different types of results. A maximum power gain can be achieved by training with the mass value corresponding to Pmax. An athlete wishing to improve speed will preferably train within the training zone V, i.e. with a light mass lifted with less than 10% of the maximum power. The zone PV (power and speed) corresponds to lighter masses than the optimum mass and require at least 90% of the maximum power. PF (power force) also requires between 90 and 100% of the maximum power, but with heavier masses. A muscular hypertrophy for body-building enthusiasts will be achieved by lifting heavy loads slowly, the developed power being then lower than 90% of the maximum power (value range Hyp).

It can thus be seen that determining the power developed for lifting different masses makes it possible to determine the optimum training conditions for an athlete.

The software's architecture thus allows the user to choose between several simple tests that are quick to execute and that supply physiological information enabling athletes or coaches to improve the training regimen. The software makes it possible to calculate and display values obtained from simple tests regardless of the type of sport for which the athlete is training.

Figure 4:
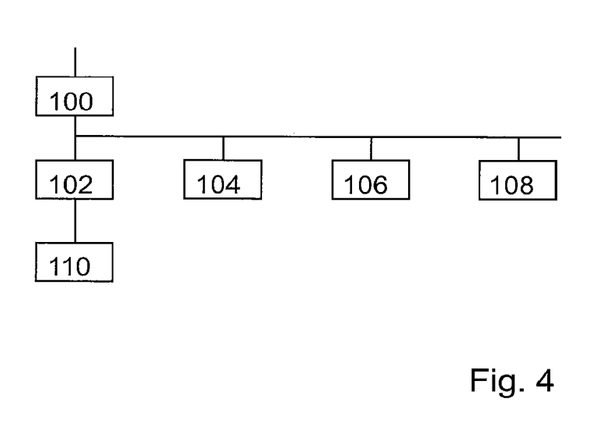
FIG. 4 is a flow diagram of the initial steps of the program executed by the inventive accelerometer.

FIG. 4 is a flow diagram illustrating the initial steps executed by the programmed device 16 after the accelerometer has been powered up. During the step 100, the device 16 executes a start-up routine that leads to the menu illustrated in FIG. 1 being displayed. The user can select during the following steps 102 to 108 one of the menu positions 51 to 54 to execute an action. The menu positions illustrated in the Figure can be replaced by corresponding icons.

By selecting, during the step 102, the menu position 51, the user is invited to select a test and then to carry out this test. The corresponding routine 110 will be described in more detail in relation to FIG. 5.

The choice of the menu position 52 (step 104) allows the previously saved measurement results to be inspected. The user can thus check his previous performances or those of other users recorded in the system.

The menu position 53 (selected during the step 106) allows the general parameters of the accelerometer to be entered or modified, for example the menu language, the date, the time, the choice of unit (metric or ounces/pounds), etc. The modifications are preferably effected by entering a choice from a list by means of the elements 13A, 13B.

The menu position 54 (step 108) allows the parameters specific to the users to be entered and modified. The system preferably enables several users with their associated parameters to be recorded; the users are identified before each use and the measurement results are associated and saved in relation to each user. During the step 108, the user can enter parameters specific to each user such as:

User's name, pseudonym or number
Sex
Weight
Height
Category (amateur, beginner, professional, etc.)
Possibly other preferences (weight of the barbells, etc.)

These parameters are preferably independent of the tests and can be stored in memory positions, for example in a Flash memory, then used for calculations associated to different types of tests.

Figure 5:
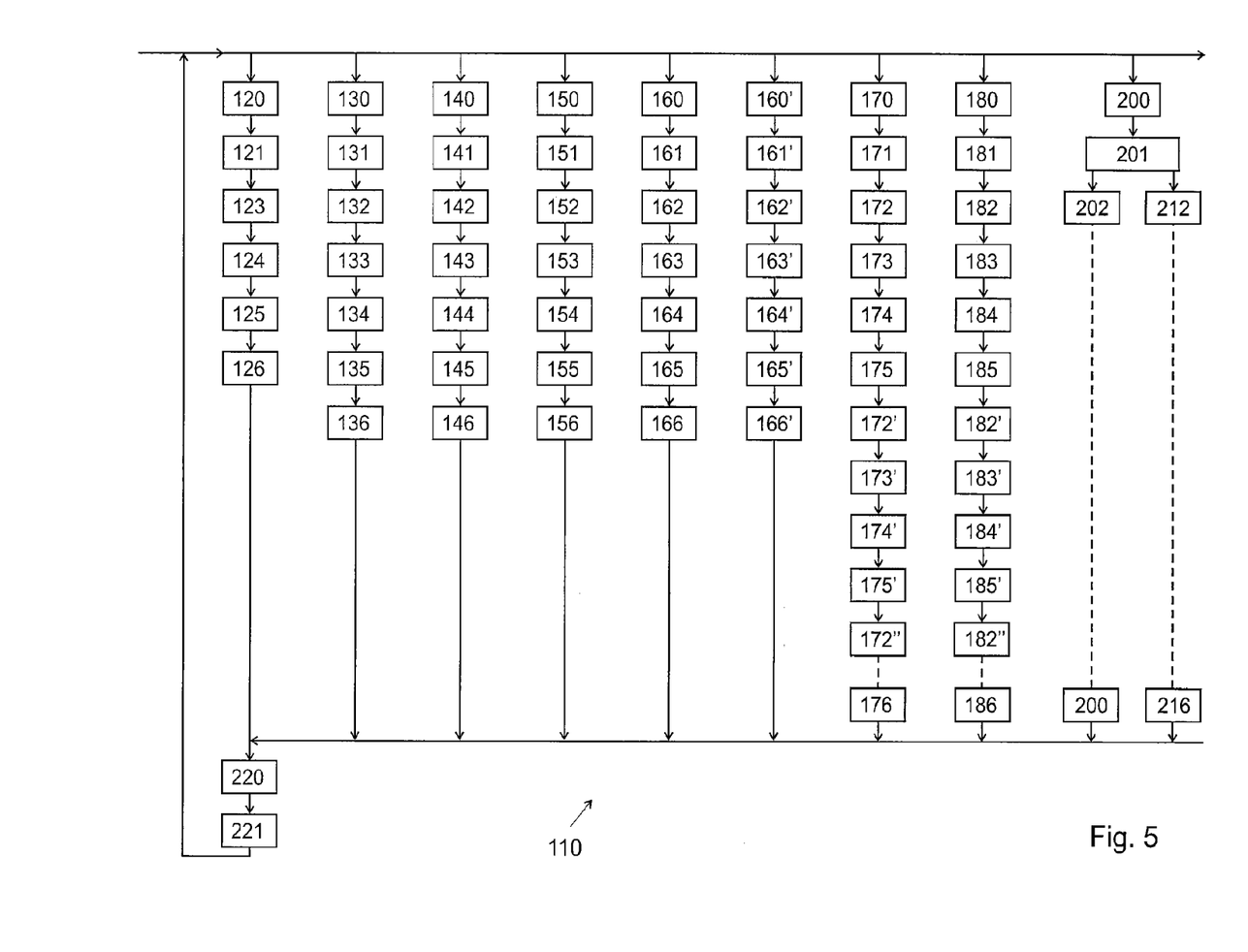
FIG. 5 is a flow diagram of the program executed by the inventive accelerometer depending on the test selected.

When the user chooses the menu position 51 to perform a test, he is invited during the step 110 to select, from a list and by means of the elements 13A, 13B, the type of test he wishes to carry out. FIG. 5 illustrates in more detail the procedure for the tests the user is invited to perform after having chosen the menu position 51.

Step 120 is initiated when the user selects the general training test. The sensor is connected to the athlete or to the displaced load in a manner that depends on the test actually performed. This menu position is intended notably for measuring several not very specific physiological parameters from tests that are not the object of a specific menu.

During the step 121, a message on the display 11 invites the user to wait until the reference to the vertical axis given by gravitation has been correctly taken. The test then starts by pressing on the button 13B (step 123). The tests starts after pressing this button only if the accelerometer is held still during at least three seconds in a vertical position, used for orienting the accelerometer correctly in space in order to determine the vertical direction. In the opposite case, an error signal is emitted if the athlete does not remain still for at least three seconds.

The beginning of the measurement is signaled to the user by an acoustic signal, for example a long beep, that invites him to begin the appropriate test. Using acoustic signals makes it possible to forgo the necessity of looking at the screen during the exercises.

In this test, acceleration data along the vertical direction are obtained at a rate of 200 or 500 Hertz (step 125), the rate being possibly modifiable in the general parameters or adapted to the available memory. The end of the measurements is signaled by an acoustic signal, for example a repeated beep. In this test, the accelerometer determines that the test is finished when the user presses again on the button 13B or at the latest after a determined period of time, for example 30 seconds during a sampling at 500 Hertz or 60 seconds during a sampling at 200 Hertz (according to the parameters chosen by the user). The test is also interrupted with an error signal if the accelerometer detects improbable accelerations.

At the end of the measurements (step 126), the values calculated during and/or at the end of the measurements are displayed on the screen 11. This test can use the weight of the identified user, or the lifted mass, to compute the concentric force, the speed of the movement and the power expended by the user during the test, and for then displaying the maxima of these three values. Indications as to the progress possibly achieved since the last saved tests can be displayed, as well as grades or appreciations on the athlete's performance (good level, experienced, etc.).

As for the other tests, the program then asks during step 220 whether the user wishes to save (step 221) the measurement results. In a preferred embodiment, only the calculated results are saved in order to cut down on memory space. It is however also possible to save the complete sequence of acceleration data, obtained during the test, and/or the results of intermediate calculations. Storing all the acceleration values makes it possible for example to transfer these data towards an external computer and perform new calculations or a more elaborate processing, or to display graphically the sequence of acceleration data or other values obtained.

The steps 130 to 136 correspond to the selection of the bench-press test. In this test, the user lies on the back and uses the arms to lift weights once or several times. The accelerometer is preferably fastened on the barbell's bar.

After selection of the test 130, indications are displayed during step 131 to invite the user to position the accelerometer correctly and then to enter the mass of the lifted weights (step 132). The mass is preferably selected by means of the buttons 13A, 13B from a pre-established multiple-choice list. In a variant embodiment, the user can increment or decrement the value of the proposed mass with the buttons 13A, then confirm the selected value by means of the button 13B.

The test then starts during step 133 when the user presses on the button 13B and provided the accelerometer then detects a movement (when the user grasps the barbell) followed by three seconds of remaining motionless.

The beginning of the data acquisition is signaled to the user by displaying a message of instructions inviting the user to grasp the bar and then remain still. An error message is emitted after 5 seconds if the accelerometer did not remain motionless during at least three consecutive seconds. In the contrary case, an acoustic signal, for example a long beep, is emitted to invite the athlete to begin the proposed test and to lift and then put down the weights five times in succession. Appropriate instructions are displayed.

The orientation of the accelerometer relative to the vertical is determined during the three seconds of inaction.

An acoustic signal is preferably emitted between each movement, while the user has put down the bar during one second, as an invitation to execute the next movement.

In this test, the acceleration data along the vertical direction are preferably obtained at a rate of 200 Hertz (step 135). The end of the measurements is signaled after the last movement has been completed by means of an acoustic signal, for example a repeated beep. The test is interrupted before the end of the test with an error signal for example if the user leaves the weights motionless for more than five seconds during two movements or if the displacements are not directed in the expected direction (for example because the test did not start from the low position) or if the number of cycles is less than 5 or also if the displacement takes more than five seconds.

Once the measurements have been completed (step 136), values computed during and/or at the end of the measurement are displayed on the screen 11. This test uses the weight of the barbells for calculating and displaying the pulse power, the average speed of movement and the average concentric force used by the athlete during the test. In a preferred embodiment, the averages are calculated over the three best movements in a series of five, i.e. the three movements during which maximum pulse power has been used. Trends can be displayed, for example by means of arrows, to indicate the progress as compared with the recorded results of previous tests. The user can store these results.

The steps 140 to 146 correspond to the selection of the half-squat test that allows the muscle groups of the legs and pelvis to be tested. The athlete must bend his knees and rise again with an upright back five times; the accelerometer is fastened against the torso or on a barbell lifted by the athlete. The test is performed in a manner similar to that of the bench-press described in connection with the elements 130 to 136 of FIG. 5. Similar results are calculated and then displayed during step 146, taking into account the athlete's weight and any additional weight lifted by the athlete.

The steps 150 to 156, 160 to 166 and 160' to 166' illustrate three jump tests. The steps 150 to 156 correspond to the selection of a plyometric (reactivity) test in order to measure the athlete's abilities of explosive power and elastic strength. The user must for example execute a vertical jump without bending the knees and from an upright standing position.

The steps 160 to 166 correspond on the other hand to the selection of a vertical countermovement jump: the user is allowed to bend the knees before the extension that will propel him vertically.

The steps 160' to 166' by contrast serve to measure the non-plyometric standing jump of a user who begins the test with knees bent at 90° and then maximum upwards thrust. The hands rest on the hips to avoid using the arms. This test is called "squat jump".

Other kinds of jumps can be provided.

In all jump tests, the frequency of acquisition is preferably high, for example 500 Hertz. The type of selected jump is displayed during the step 151, 161 resp. 161'. During the step 152 (resp. 162; 162'), the user's previously recorded weight is displayed; the user is given the possibility of incrementing or decrementing it with the buttons 13A, 13B. The user is then invited to press on a button to start the test (step 153/163/163'), which then begins with an acoustic signal as soon as a period of inaction of three seconds has been detected (154/164/164').

The user is then invited to execute five vertical jumps in the conditions corresponding to each test (155/165/165'). The test is interrupted with an error message if the number of jumps is less than five, or if the accelerometer remains immobile for several seconds between two jumps, or if the duration of the jumps is too long. Furthermore, in the countermovement jump test, an error message is also emitted if no vertical downward movement is detected when the user is supposed to gain momentum at the beginning of each movement. By contrast, in the squat jump test, an error message is emitted if a vertical downward movement is detected before the jump. In the plyometric test, another error message is generated if the contact time on the ground is greater than 0.25 seconds. Furthermore, an acoustic signal can be emitted between each movement.

The test results are calculated and displayed during the steps 156 resp. 166 or 166'. The accelerometer computes and possibly displays the following parameters:
Number of executed movements (jumps); as mentioned, an error signal is emitted if the athlete does not perform the required number of jumps during the given predetermined time.

For the plyometric test, the accelerometer computes and preferably also displays the following values:
Flight time between each jump/average flight time/maximum flight time
Contact time on the ground between each jump
Height achieved, averaging the heights over the five jumps
Average over three to five movements of muscular stiffness S, defined as being:

$S=$(force at zero speed) divided by the distance of the downward movement

Average over three to five movements of the reactivity index R, defined as being:

$R=$(flight time)$^2$/duration of contact on the ground

In the case of a vertical jump with momentum, the following values will be computed and preferably displayed:
The maximum speed and height of flight and the average of these values over all or only the three best jumps
The braking power BP for each jump and the average of the braking power over all or only the three best jumps
The upward pumping power PP for each jump and the average of the pumping power over all or only the three best jumps
The power ration PR=PP/BP Other values can be displayed for each type of jump, including average or maximum speed, trends, etc. Averages and maxima can be calculated on the basis of the better jump(s), of all the jumps or of all the jumps except the first and/or last.

In the case of vertical squat jump, the following values will preferably be calculated:
The maximum speed and flight height and the average of these values over all or only the three best jumps
The impulse power IP for each jump and the average of the impulse power over all or only the three best jumps
The upward pumping power PP for each jump and the average of the pumping power over all or only the three best jumps
The power ratio PR=PP/BP Other values can be displayed for each type of jump, including average or maximum speed, trends, etc. Averages and maxima can be calculated on the basis of the better jump(s), of all the jumps or of all the jumps except the first and/or last.

The steps 170 to 176 illustrate a more complex test performed to obtain a bench-press profile in order to measure physiological values on muscle groups linked to the arms. In this test, the user executes several (for example eight) weight-lifting movements as in the test 130-136 but using a variable weight between each movement. The initial weight and the variation in weight between each movement depend on the users' level (determined for example by means of previous tests), of their gender and possibly their weight or other parameters.

The steps 170 to 174 correspond respectively to the steps 120 to 124 of the ordinary bench-press test, only the indications displayed during the step 171 are different. During step 175, the user must lift the weight only once instead of the five times required in test 125. It is also possible to lift the weight several times in test 175.

At the end of the movement 175, instead of displaying the results immediately, the user is invited to modify the weight (172'), to confirm the replacement value with the button 13B (173') and to execute the exercise again (175') after the acoustic signal 174'. The complete process is repeated several times, for example eight times, with weights that vary each time. The results of the complete test are then computed and displayed during the step 176.

The computed and/or displayed results include for example:
- The number of executed movements
- The maximum power PMax, obtained for example by means of an interpolation by polynomial approximation of the average or maximum power values of each movement
- The optimum weight with which the athlete should train in order to develop the power PMax according to the curve illustrated in FIG. 3
- The maximum weight the athlete would be able to lift at a given minimum speed, for example 10 cm/s
- The maximum resistance
- The limits of the ranges V, PV, PF, Hyp in FIG. 3
- Etc.

The steps 180 to 186 correspond to the selection of the "half-squat profile" in order to measure physiological values on muscle groups linked to the legs. The test is conducted in a manner similar to that described in relation with the steps 170 to 176, but the user is invited to execute several half-squat movements by lifting variable weights, instead of a series of bench-presses. The results computed and then displayed are for example the same as for the bench-press profile.

The steps 200 to 216 correspond to the execution of tests defined by the user and loaded for example via an interface from an external computer. New tests can be programmed by the user by means of an appropriate program on a PC and/or downloaded from Internet. The definition of the tests is determined for example by an XML file or by another data structure suitable for defining the emitted visual and acoustic messages, the computed and displayed values, etc. In one embodiment, tests can also be created and modified from the accelerometer 1.

After having made the selection 200, the user is invited to choose which of the programmed test from a list of previously installed tests is to be performed. In the example, the choice is between two additional tests starting with the steps 202 and 212. The following steps will depend on the programming but typically ends with the results being displayed during the steps 206 resp. 216, with the computed and displayed values being also determined by the file downloaded from the external computer.

In the above examples, the end of the test and the switch to the calculation and display of the results is determined automatically after execution of a number of movements (for example a weight lift or a jump) depending on the test. The complete execution of a movement can be determined from the data obtained by the accelerometer (for example by detecting that the accelerometer is immobile) or after a predetermined lapse of time that can also depend on the test. It is possible to provide tests of predetermined duration, for example tests consisting in performing the maximum number of jumps, lifts or core muscle strengthening exercises within a given time.

Most of the tests described by way of example here above comprise several movements preceded and separated by intervals during which the accelerometer is immobile. An error signal can be emitted if the accelerometer is not immobile. It is also possible to use these phases to calibrate the vertical position of the accelerometer in order to calculate accelerations and other values exclusively in the vertical direction or in the direction of displacement of the weight. In a preferred embodiment, these phases of inaction are also used for re-initializing the speed and/or the position of the accelerometer in order to avoid the accumulation of errors due to integration.

The initial selection of the type of test the user wishes to perform determines for example the following parameters:
- Acquisition rate of the acceleration data as well as number of bits used
- Initial indications displayed to the user at the beginning of the test and/or during the test and/or between different movements
- Parameters that need to be entered by the user and/or read from a memory area
- Acoustic signals reproduced at the beginning of the test and/or during the test and/or between different movements
- Conditions for starting the acquisition
- Conditions that will generate an error and/or interrupt the acquisition during a test
- Conditions that will determine the end of a test and/or the end of a movement in a test comprising several movements
- Profile of measured or computed values during the test, this profile being usable for example to generate errors if the acquired data do not match expectations
- Values calculated during the tests and/or between two movements of a test and/or at the end of a test
- Values displayed during a test and/or at the end of a test
- Values stored in the memory
- Etc.

None of these parameters is essential. It is thus possible to implement procedures in which any kind of subcombination of parameters depends on the selected test.

The invention claimed is:

1. A method carried out by a portable accelerometer for obtaining physiological muscle values of a user by means of the portable accelerometer, comprising:
   selecting by the user of a type of a test to be carried out from a plurality of tests, wherein one type of test comprises performing a series of jumps;
   measuring a sequence of acceleration data during the test;
   emitting a first sound signal after the execution of each jump from the series of jumps in order to invite the user to execute a next jump;
   displaying on a display of said portable accelerometer a value calculated based on successive measurements of the sequence of acceleration data,
   re-initializing a speed during at least one phase of standstill between two jumps, and
   determining automatically an end of the test,
   wherein the end of the test depends on at least one of a complete execution of a predetermined number of jumps, and lapsing of a predetermined period of time.

2. The method of claim 1, wherein the accelerometer is programmable.

3. The method of claim 1, wherein the end of the test depends on execution of a pre-determined number of movements with variable loads.

4. The method of claim 1, wherein the end of the test depends on lapsing of a period of time which is dependent on selected type of the test.

5. The method of claim 1, wherein the frequency of acquisition of the acceleration depends on the type of test selected.

6. The method of claim 1, wherein an error signal is emitted when a value obtained from the sequence of measured acceleration values does not correspond to a pattern dependent on the type of text selected.

7. The method claim 1, wherein a calculation dependent on the type of test selected is performed from said acceleration data, and wherein a value dependent on the type of test selected is displayed during or at the end of the test.

8. The method of claim 1, including a step during which at least one parameter dependent on the type of selected test is required from the user or read from a memory position.

9. The method of claim 1, wherein a sequence of speed data is determined during the test by integration of said sequence of acceleration data, the speed being re-initialized at least once during the test when the accelerometer determines that the speed is zero.

10. The method of claim 9, said test including several movements separated by phases of standstill, the speed being re-initialized during said at least one standstill phase.

11. The method of claim 1, including a step of determining the maximum force or the average force from said acceleration data multiplied by a mass parameter entered by the user.

12. The method of claim 11, including a step of determining the maximum power or the average power from the strength and the speed.

13. The method of claim 1, including a step of determining the height of a jump and/or the duration of a flight from said sequence of acceleration data.

14. The method of claim 1, including a step of determining the muscle explosiveness from said sequence of acceleration data.

15. A method carried out by a portable accelerometer for obtaining physiological muscle values of a user, wherein the method comprises the following operations:
   inviting by the portable accelerometer the user to perform a number of successive jumps;
   measuring by the portable accelerometer a sequence of acceleration data during each of said successive jumps;
   determining by the portable accelerometer a sequence of speed data by integrating said acceleration data;
   emitting by the portable accelerometer a first sound signal afer the execution of each of said successive jumps, in order to invite the user to execute a next jump;
   re-initializing by the portable accelerometer the speed during at least one phase of standstill between two jumps;
   automatically determining by the portable accelerometer the end of the test after a predetermined number of jumps;
   emitting by the portable accelerometer a second sound signal different from the first signal, in order to indicate the end of the test; and
   displaying by the portable accelerometer a plurality of values calculated on the basis of said sequence of acceleration data.

16. The method of claim 15, said values comprising the force and power of the user.

17. A portable accelerometer for measuring tri-axial physiological values, comprising:
   an acceleration sensor;
   a display;
   an electric battery;
   a plurality of elements enabling parameters and/or a plurality of commands to be entered manually;
   a programmed device for inviting a user to select, by means of said plurality of elements, a type of a test from among several predefined tests,
   wherein one type of the test comprises performing a series of jumps,
   wherein the portable accelerometer is capable of emitting a first sound signal after the execution of a jump from the series of jumps, in order to invite the user to execute a next jump;
   wherein the portable accelerometer is capable of re-initializing a speed during at least one phase of a standstill between two jumps;
   wherein the portable accelerometer is capable of automatically determining the end of the test after a predetermined number of jumps and/or lapsing of a predetermined period of time;
   wherein the portable accelerometer is further capable of emitting a second sound signal different from the first signal, indicating the end of the test.

18. The accelerometer of claim 17, wherein said acceleration sensor is capable of measuring the acceleration along one or several axes.

19. The accelerometer of claim 17, comprising an interface for connecting it the accelerometer to an external computer in order to load new tests.

20. A portable accelerometer for measuring physiological muscle values of a user, comprising:
   a computer program for inviting the user to perform a plurality of successive jumps;
   an accelerometer digitally controlled for measuring a sequence of acceleration data during each jump of said plurality of successive jumps;
   a digitally controlled loudspeaker arranged for generating a first sound signal after the execution of each jump of said plurality of successive jumps, in order to invite the user to execute a next jump; and a second sound signal different from said first signal at indicating the end of the test;
   a digitally controlled display arranged for displaying a plurality of values calculated on the basis of said sequence of acceleration data,
   wherein the portable accelerometer is capable of re-initializing a speed during at least one phase of a standstill between two jumps, and
   wherein the portable accelerometer is capable of automatically determining the end of the test after a predetermined number of jumps and/or lapsing of a predetermined period of time.

* * * * *